US012631557B2

(12) United States Patent
James et al.

(10) Patent No.: US 12,631,557 B2
(45) Date of Patent: May 19, 2026

(54) EQUILIBRIUM PLASMONIC ANALYTE SENSING APPARATUS AND METHODS

(71) Applicants: Jay James, Berkeley, CA (US); Jeffrey Scott Crosby, Richmond, CA (US)

(72) Inventors: Jay James, Berkeley, CA (US); Jeffrey Scott Crosby, Richmond, CA (US)

(73) Assignee: Picoyune, LLC, Berkeley, CA (US)

( * ) Notice: Subject to any disclaimer, the term of this patent is extended or adjusted under 35 U.S.C. 154(b) by 351 days.

(21) Appl. No.: 18/071,597

(22) Filed: Nov. 29, 2022

(65) Prior Publication Data

US 2024/0159671 A1    May 16, 2024

Related U.S. Application Data

(60) Continuation-in-part of application No. 17/197,805, filed on Mar. 10, 2021, now Pat. No. 11,898,957, which is a continuation of application No. 16/807,374, filed on Mar. 3, 2020, now Pat. No. 10,976,252, which is a division of application No. 16/377,124, filed on Apr. 5, 2019, now Pat. No. 10,620,122.

(Continued)

(51) Int. Cl.
*G01N 21/552* (2014.01)
*G01N 33/00* (2006.01)

(52) U.S. Cl.
CPC ....... *G01N 21/554* (2013.01); *G01N 33/0045* (2013.01)

(58) Field of Classification Search
CPC ............. G01N 21/554; G01N 33/0045; G01N 21/0332; G01N 21/05; G01N 21/553
See application file for complete search history.

(56) References Cited

U.S. PATENT DOCUMENTS 7,456,972 B2 * 11/2008 Ke ........................ G01N 21/648
356/448
7,486,400 B2 * 2/2009 Saito .................... G01N 21/554
356/301

(Continued)

FOREIGN PATENT DOCUMENTS

EP            3121587 A1 * 1/2017 .......... G01N 21/554

*Primary Examiner* — Michelle M Iacoletti
(74) *Attorney, Agent, or Firm* — Jeffery Frazier

(57) ABSTRACT

Apparatus and methods are provided for quantitative detection of mercury vapor in gas samples using a film of nanoparticles. The localized surface plasmon resonance (LSPR) of an amalgam nanoparticle is sensitive to adsorbed mercury mass. The equilibrium mass of mercury on a gold nanoparticle is a function of the surrounding vapor concentration and the temperature of the gold. A device that introduces a temperature-controlled gold nanoparticle film to a controlled flow of sample gas responds predictably to a given mercury vapor concentration when optically probed in situ. Controlling the temperature of the film allows for control of adsorption and desorption rates. Equilibrium plasmonic mercury detection, described herein, removes the cycling necessary for many gold-based mercury analyses. Methods are given for the operation and analysis of the temperature-stabilized gold nanoparticle mercury sensor. The disclosed mercury-detection apparatus and methods find use in a variety of applications, including, for example, mercury detecting applications.

18 Claims, 7 Drawing Sheets

Related U.S. Application Data

(60) Provisional application No. 63/283,989, filed on Nov. 29, 2021, provisional application No. 62/653,555, filed on Apr. 5, 2018.

(56) References Cited

U.S. PATENT DOCUMENTS

| | | | | |
|---|---|---|---|---|
| 9,291,557 | B2 * | 3/2016 | James | G01N 33/0045 |
| 9,322,823 | B2 * | 4/2016 | Denomme | G01N 21/554 |
| 10,620,122 | B2 * | 4/2020 | James | G01N 21/0332 |
| 10,794,904 | B2 * | 10/2020 | Denomme | G01N 33/54346 |
| 2006/0197952 | A1 * | 9/2006 | Chen | G01N 21/554 |
| | | | | 356/445 |
| 2006/0197953 | A1 * | 9/2006 | Perez | B82Y 15/00 |
| | | | | 356/445 |
| 2008/0037022 | A1 * | 2/2008 | Nishikawa | G01N 21/554 |
| | | | | 977/773 |
| 2011/0267621 | A1 * | 11/2011 | Nakatani | G01N 33/54373 |
| | | | | 438/16 |
| 2012/0021524 | A1 * | 1/2012 | Van Hal | G01N 27/12 |
| | | | | 436/81 |
| 2012/0188551 | A1 * | 7/2012 | Langhammar | G01N 21/554 |
| | | | | 356/445 |
| 2012/0257198 | A1 * | 10/2012 | Yamada | G01N 21/658 |
| | | | | 356/301 |
| 2012/0257204 | A1 * | 10/2012 | Walters | G01R 3/00 |
| | | | | 438/66 |
| 2012/0327417 | A1 * | 12/2012 | Amako | B82Y 20/00 |
| | | | | 977/773 |
| 2013/0182258 | A1 * | 7/2013 | Amako | G01N 21/554 |
| | | | | 428/141 |
| 2014/0333933 | A1 * | 11/2014 | James | G01N 21/554 |
| | | | | 356/432 |
| 2015/0124258 | A1 * | 5/2015 | Amako | G01N 21/658 |
| | | | | 977/954 |
| 2019/0310192 | A1 * | 10/2019 | James | G01N 21/554 |

* cited by examiner

EQUILIBRIUM PLASMONIC ANALYTE SENSING APPARATUS AND METHODS

CROSS-REFERENCE TO RELATED APPLICATIONS

This application is a continuation-in-part (CIP) of U.S. patent application Ser. No. 17/197,805 filed Mar. 10, 2021, which is a continuation of U.S. patent application Ser. No. 16/807,374 filed Mar. 3, 2020, which issued as U.S. Pat. No. 10,976,252 on Apr. 13, 2021 and is a divisional of U.S. patent application Ser. No. 16/377,124 filed Apr. 5, 2019, which issued as U.S. Pat. No. 10,620,122 on Apr. 14, 2020 and claims the benefit of priority from U.S. Provisional Patent Application No. 62/653,555 filed Apr. 5, 2018; each of which is incorporated herein by reference in its entirety. This application claims the benefit of priority from U.S. Provisional Patent Application No. 63/283,989 filed Nov. 29, 2021; which is incorporated herein by reference in its entirety.

FIELD

The present teachings relate to apparatus and methods for the detection of analytes, such as mercury, in test samples.

INTRODUCTION

Mercury (Hg) is a pollutant of global concern that can negatively affect human and ecosystem health. Improved sensing apparatus and methods are desirable to aid efforts aimed at reducing mercury exposure and poisoning.

Gold nanoparticle films have a localized surface plasmon resonance (LSPR), with strong optical absorbance in the visible band. The resonant peak depends on the size, shape, and composition of the particles. Gold also exhibits a natural affinity for mercury, which readily adsorbs onto the surface of the particles. Mercury participates in the surface plasmon resonance, shifting the optical absorbance peak of the amalgam mercury-gold particles. The magnitude of this shift is proportional to the mass of mercury on the nanoparticles; furthermore, the adsorption of mercury is proportional to the concentration of mercury vapor in contact with the nanoparticle film as mediated by the sorption and desorption rate for mercury on the amalgam nanoparticles. This proportionality provides a means by which a transducer can be constructed from gold nanoparticle films.

To a first approximation the adsorption can be modeled by a Langmuir Isotherm at equilibrium:

$$\theta = \frac{C}{\dfrac{k_d}{k_a} + C}$$

where $\theta$ is the surface coverage, C is the concentration of mercury above the surface and $k_d$ and $k_a$ are the desorption and adsorption constants respectively. The adsorption and the desorption rate constant are dependent on the surface temperature; at higher temperatures $k_d$ is higher and $k_a$ is generally lower in magnitude. Raising the temperature means for a given concentration a smaller proportion of the surface is covered at equilibrium.

A known LSPR-based system for detecting mercury utilizes a combination of a trap and detector. In the known system, mercury in a sample accumulates on a gold nanoparticle film, which acts as a trap, and the rate of change in the LSPR signal is proportional to the concentration of Hg in the gas. The film is then heated to a high temperature to purge the mercury from the gold nanoparticles in a regeneration step. (See, e.g., U.S. Pat. No. 9,291,557 to James et al., incorporated herein by reference in its entirety.)

Advantageously, according to various embodiments, apparatus and methods for plasmonic mercury detection of the present disclosure do not require regeneration. In accordance with various embodiments, as described herein, the steady state LSPR signal of an amalgam nanoparticle film corresponds to the mercury concentration of the surrounding gas.

SUMMARY

An exemplary and non-limiting summary of various embodiments is set forth next.

Various aspects of the present disclosure relate to mercury-sensing detectors, or detection systems based on surface plasmon resonance (SPR) for detecting trace mercury in samples. In various embodiments, for example, a mercury detector comprises a flow cell that includes a mercury-sensitive film therein. The mercury-sensitive film can comprise, for example, a plurality of metallic nanoparticles disposed on a surface of a substrate. The particular metallic material employed depends, for example, on the tested-for analyte. For example, to detect mercury, various embodiments of the present disclosure contemplate the use of gold nanoparticles. In various embodiments, for example, a plurality of gold nanoparticles are disposed on a surface of a substrate. In some embodiments, the nanoparticles comprise gold and mercury amalgam nanoparticles.

In various embodiments, prior to exposure to mercury vapor samples the nanoparticle film is in a condition where any additional mercury adsorption is reversible by contact to mercury free gas. In accordance with various embodiments, this initial condition requires a specific nanoparticle size and composition for a given operating temperature.

In accordance with various embodiments, a mercury-sensitive film comprising gold and mercury amalgam nanoparticles is pre-conditioned to substantially preclude or otherwise exhibit substantially no irreversible mercury adsorption during use at a selected sample-testing operating temperature. In various embodiments, for example, a specific amalgam condition of gold nanoparticles is established via a pre-conditioning protocol. According to various embodiments, such a pre-conditioning protocol can comprise, for example, the steps of: holding the film steady at the selected operating temperature and exposing it to sufficient gaseous mercury so as to fill or saturate substantially all irreversible mercury adsorption sites; and then, permitting any excess mercury to desorb during a period of mercury-free gas flow.

In accordance with various embodiments, a substrate for supporting a mercury-sensitive film is optically clear or transparent. In some embodiments, a region (e.g., back portion) of the substrate is mirrored.

In various embodiments, a mercury detector of the present disclosure can further comprise a light source and a light detector. In various embodiments, for example, the light source comprises a visible light source, such as one or more light-emitting diodes (LEDs). In some embodiments, the light detector comprises one or more filtered photodiodes.

According to various embodiments, a mercury detector can further comprise a temperature controller including a heater and a temperature sensor. In various embodiments, for example, the heater and temperature sensor are configured to heat the mercury-sensitive film to a selected temperature that is elevated with respect to an ambient temperature (where ambient temperature, for example, typically falls within a range of from about 20 degrees Celsius to about 25 degrees Celsius; e.g., 22 degrees Celsius or 23 degrees Celsius) and to maintain such temperature substantially constant over a period. In some embodiments, a heater and temperature sensor are disposed in contact with the substrate for keeping the film at an elevated temperature that is largely constant.

In various embodiments, the nanoparticles cover an entire surface of a substrate. In other embodiments, the nanoparticles cover less than an entire surface of the substrate. For example, in some embodiments, the nanoparticles cover no more than a fractional portion of a surface of the substrate.

Nanoparticles of various geometrical shapes can be utilized. In various embodiments, for example, the nanoparticles are spherical. In some embodiments, the nanoparticles are oblong. According to various embodiments, the nanoparticles are free of surface coating.

In some embodiments, a mercury detection system according to the present teachings also includes a pressurized gas source in fluid communication with the flow cell and configured to provide a flow of gas, such as a gaseous sample or conditioning gas, through the cell.

In various embodiments, a mercury detection system according to the present teachings also includes a thermal decomposition system in communication with the flow cell and configured to provide an elemental mercury vapor from condensed samples.

Further aspects of the present disclosure relate to methods for sensing mercury using a mercury detector as described herein.

In some embodiments, two distinct (e.g., adjacently disposed) locations on the substrate are probed, one with and one without a film or layer of nanoparticles thereon, and these signals are compared to correct for background changes.

In some embodiments, one or more fluid-flow lines are connectable to the detector; for example, (i) an input line for introducing a gas, such as a gaseous sample to be tested for mercury or a mercury-free conditioning gas, and (ii) an exit line for removal of gas from the detector. In some embodiments, such an exit line can include a mercury removal filter.

In some embodiments of the mercury detection system, the system is configured to detect mercury vapor at concentrations of 18 mg/m$^3$ or less.

Further aspects of the present disclosure relate to methods for detecting mercury in a sample, such as a gaseous sample. In various embodiments, for example, such a method can comprise the steps of contacting the sample with a mercury-sensitive film, irradiating the mercury-sensitive film with light, and detecting for a change in the visible light absorbance of the nanoparticles.

In some embodiments, the contacting can include flowing a gaseous sample through a flow cell that includes the mercury sensitive film.

In some embodiments, the method can also include quantifying the amount of mercury in the sample. In various embodiments, for example, the quantifying includes determining the amount of mercury in the sample based on a detected change in the localized surface plasmon resonance of the nanoparticles. In various embodiments, the quantifying includes determining the change in absorbance (A) of the mercury sensitive film at a particular wavelength (λ) band. In some embodiments, the method includes determination of a discrete mass of mercury in a sample by integrating the change in absorbance (A) over the duration (t) of the sample exposure.

The disclosed mercury detectors and methods can find use in a variety of different applications, including, e.g., mercury detecting in environmental or industrial applications.

According to various embodiments, the sample carrier gas comprises air. In some embodiments, the sample carrier gas comprises one or more hydrocarbon compounds. In a variety of embodiments, the sample carrier gas comprises steam. In some embodiments, the sample carrier gas comprises the exhaust of a sample decomposition furnace.

In accordance with various embodiments, light detection takes place continuously during exposure of the mercury-sensitive film to mercury vapor.

In some embodiments, the magnitude of the intensity change is correlated to the concentration of mercury in a test sample by comparison with a calibration performed with a quantified mercury vapor source.

In some embodiments, the rate of change of magnitude of the intensity change is correlated to the concentration of the mercury by comparison with a calibration performed with a quantified mercury vapor source.

In some embodiments of the method, the calibration of change in absorbance of the film to mercury concentration is nonlinear.

In some embodiments, the method includes optically probing a plurality of points of the film.

In some embodiments, the method includes quantification of the change in absorbance of the nanoparticle film to the change in absorbance of an adjacent section of the substrate without nanoparticle film coating.

In some embodiments, mercury free gas is passed over the film to adjust the zero setting of the calibration.

In some embodiments, the sensor is calibrated with injections of known masses of mercury.

In some embodiments the method includes removing mercury from the sample stream with a trap and setting the zero for the detector.

Various aspects of the present teachings relate to a mercury detector or detection system. According to various embodiments, a mercury detector or detection system of the present teachings can comprise, for example: (a) a flow cell comprising a mercury sensor, wherein the mercury sensor comprises: (i) a transparent substrate; and, (ii) a mercury-sensitive film on a surface region of the substrate, wherein the mercury-sensitive film comprises a plurality of gold-mercury amalgam nanoparticles; (b) a light source configured for directing light through the transparent substrate to the mercury-sensitive film; (c) a light detector configured for detecting a localized surface plasmon resonance (LSPR) signal from the mercury-sensitive film; and, (d) a temperature-control unit for maintaining the mercury-sensitive film at a substantially constant selected temperature; wherein the system determines whether mercury is present in a sample based on a LSPR signal detected from the mercury-sensitive film. In various embodiments, a mercury detector of the present teachings can further comprise a gas source in communication with the flow cell and configured to provide a flow of a gas through the flow cell.

In various embodiments, the detected signal is continuous, and the temperature of the film is steady state. According to various embodiments, the detected signal comprises an equilibrium signal or a signal that comes into equilibrium.

According to various embodiments, the sample can comprise a gaseous sample.

In various embodiments, the light source comprises a visible light source.

In various embodiments, a mercury detector or detection system can be configured to detect changes in optical absorbance in a single active band of visible light spectrum.

In accordance with various embodiments, the light detector comprises a photodiode, such as a standard photodiode. In various embodiments, the photodiode comprises a UV-Vis photodetector.

In various embodiments, the gold-mercury amalgam nanoparticles can be substantially spherical in shape and can have an average diameter within a range from 1 nm to 20 nm.

According to various embodiments, the transparent substrate includes a second surface region that is substantially free of mercury-sensitive film. Further, in some embodiments, the light source is configured for additionally directing light through the transparent substrate to the second surface region. As well, in some embodiments, the detector is configured for additionally detecting a second signal from the second surface region. Additionally, in some embodiments, the system is configured to determine a ratio comprising signal detected from the mercury-sensitive film and signal detected from the second surface region that is substantially free of mercury-sensitive film.

In accordance with various embodiments, the nanoparticles of the film are preconditioned to substantially preclude irreversible mercury adsorption/desorption during use with a sample at the selected temperature, such that the nanoparticle film is substantially precluded from irreversibly gaining or losing mercury.

In various embodiments of the present teachings, a mercury detector or detection system (e.g., an LSPR flow sensor) of the present teachings can comprise, for example: a flow cell; a nanoparticle film inside the flow cell; and, a temperature-control unit for maintaining the nanoparticle film at a selected constant temperature.

In various embodiments, the nanoparticle film comprises gold nanoparticles. In accordance with various embodiments, the nanoparticle film comprises gold and mercury amalgam nanoparticles.

Further aspects of the present teachings relate to a method of analysis using a sensor such as the foregoing, where mercury is detected based on the location of an LSPR peak. In various embodiments, the LSPR peak measured by monitoring changes in transmission through the nanoparticle film in a single band of visible spectrum. According to various embodiments, the LSPR signal location is related to the mercury vapor concentration through a combination of position and time derivative (approximating velocity). In various embodiments, the LSPR signal location is related to mercury concentration monotonically but non-linearly. In various embodiments of a method of analysis using a sensor such as the foregoing, mercury is detected based on an integration of the change in LSPR peak with time.

Further aspects of the present teachings relate to a method for determining whether mercury is present in a gaseous sample. In various embodiments, a method of the present teachings can comprise, for example: (a) contacting a sample to a mercury sensor comprising: (i) a transparent substrate; and, (ii) a mercury-sensitive film on a surface region of the substrate, wherein the mercury-sensitive film comprises a plurality of gold-mercury amalgam nanoparticles; (b) maintaining the mercury-sensitive film at a substantially constant selected temperature; (c) while performing step (b): (i) directing light through the transparent substrate to the mercury-sensitive film, and, (ii) detecting a localized surface plasmon resonance (LSPR) signal from the mercury-sensitive film; and, (d) determining whether mercury is present in the sample based on a LSPR signal detected from the mercury-sensitive film.

According to various embodiments, step (d) includes monitoring changes in transmission through the mercury-sensitive film in a single band of visible spectrum. In various embodiments, step (d) includes integrating detected steady-state LSPR signal with time.

In various embodiments, the detected signal is continuous, and the temperature of the film is steady state. According to various embodiments, the detected signal comprises an equilibrium signal or a signal that comes into equilibrium.

In accordance with various embodiments, the transparent substrate further comprises a second surface region that is substantially free of mercury-sensitive film, and the method further comprises additionally directing light through the transparent substrate to the second surface region while detecting for a signal from the second surface region, and then determining a ratio of signal detected from the mercury-sensitive film and signal detected from the second surface region that is substantially free of mercury-sensitive film.

In various embodiments, the nanoparticles of the film are preconditioned to substantially preclude irreversible mercury adsorption/desorption during use with a sample at the selected temperature, such that the nanoparticle film is substantially precluded from irreversibly gaining or losing mercury.

Further aspects of the present teachings relate to a nanoparticle-based mercury sensor where, in operation, the nanoparticles are held a steady temperature. In various embodiments, the nanoparticles comprise gold or an amalgam of gold and mercury. In some embodiments, the particles are substantially spherical and have a diameter within a range of from about 1 nm to about 20 nm (e.g., about 5 nm). In various embodiments, the particles are suspended on a surface of a substrate, such as a mirror-backed quartz substrate. In some embodiments, the substrate comprises one or more optical fibers.

In various embodiments, substrate-bound particles are contained within a flow cell. As contemplated herein, such a flow cell can protect the nanoparticle film. Further, such a flow cell can facilitate controlling the temperature of the film to a fairly high level of precision. Additionally, the flow cell can assist in the introduction of a sample stream to the nanoparticles of the film, e.g., by way of a nozzle. In various embodiments, a nozzle connected to a flow cell can provide for some control over the mass transfer of mercury to the nanoparticles of the film. According to various embodiments, a flow cell can facilitate in the introduction of light for interrogating the nanoparticles, and in collecting light back for analysis. In various embodiments, the flow cell isolates the sample gas from the environment. According to various embodiments, a flow cell can be configured to facilitate connection of standard tubing, such as Teflon tubing.

In various embodiments, two spots are used on the transparent substrate, with one being free of nanoparticles and one comprising a film of nanoparticles. In such embodiments, for example, the nanoparticle-free spot can provide a reference or correction for the measurement. Further, in various embodiments, the flow cell can geometrically fix the nanoparticle film with respect to the optics and temperature controller of the detector system.

In various embodiments, a detector system of the present teachings can include, for example, a pump, flow controllers, light production from a temperature-stabilized LED that has a narrow bandwidth of light, and analysis electronics.

According to various embodiments, a method is provided for operating a mercury sensor of the present teachings, wherein a sample gas stream is introduced into the flow cell in a controlled manner and the change in the plasmonic resonance absorbance band is measured in real time.

In still further of its aspects, the present disclosure relates to a process for manufacturing a mercury-sensitive film comprising a plurality of gold-mercury amalgam nanoparticles. In various embodiments, such a process can comprise, for example: (a) supporting a gold-nanoparticle film on a transparent substrate; (b) maintaining the gold-nanoparticle film at a substantially constant selected operating temperature; and, (c) while performing step (b): (i) exposing the gold-nanoparticle film to mercury vapor in air while detecting for a first localized surface plasmon resonance (LSPR) signal from the film, and allowing the first signal to stabilize; and then, (ii) exposing the gold-nanoparticle film to mercury-free air while detecting for a second LSPR signal from the film and allowing the second signal to stabilize; whereby the nanoparticles of the film are preconditioned to substantially preclude irreversible mercury adsorption during use with a sample at the selected operating temperature.

In various embodiments, the stabilization involves a change in intensity of the detected LSPR signal at certain wavelengths.

Various embodiments of the present teachings provide a product made by the foregoing process. For example, in various embodiments, a mercury-sensitive film is made according to the foregoing process.

In accordance with various embodiments, the mercury sensitive film is in a condition where mercury adsorption due to elevated concentration in the gas in contact with the film is reversible. Such can be effected, according to various embodiments, by removing mercury from the gas stream. Accordingly, in various embodiments, the film comprises an amalgam from the outset (i.e., prior to sample testing).

In various embodiments, position of the LSPR peak is directly related to the Hg concentration in the gas.

According to various embodiments, apparatus and methods of the present teachings provide for continuous operation providing an uninterrupted measurement stream from a single sensor.

The disclosed mercury detectors and methods can find use in a variety of different applications, including, for example, mercury detecting in environmental or industrial applications.

BRIEF DESCRIPTION OF THE DRAWINGS

Various embodiments of the disclosure will be discussed with reference to the following exemplary and non-limiting drawings, in which like elements are numbered similarly, and where.

DETAILED DESCRIPTION

Figure 1:
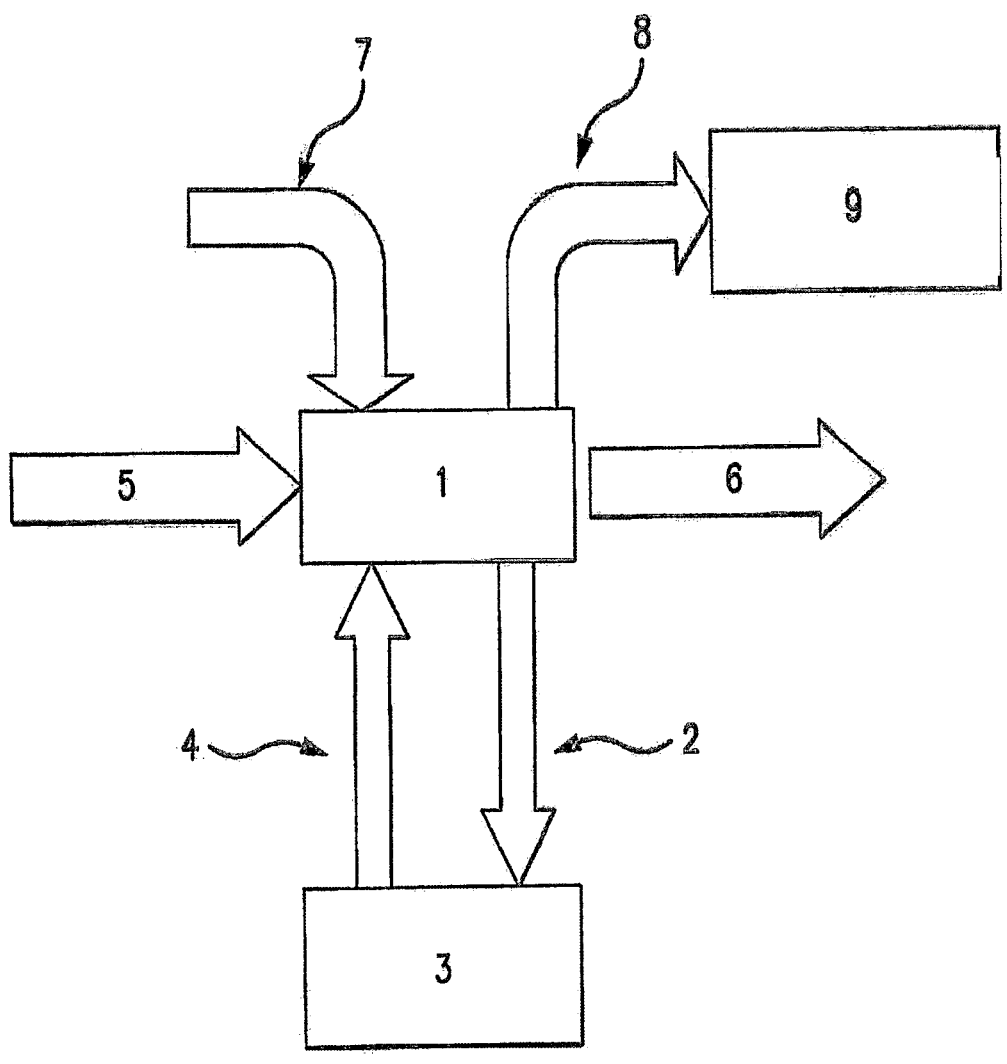
FIG. 1 is a functional block diagram of a temperature-stabilized LSPR mercury detector, according to various embodiments of the present disclosure.

Reference will now be made to various embodiments. While the present teachings will be described in conjunction with various embodiments, it will be understood that they are not intended to limit the present teachings to those embodiments. On the contrary, the present teachings are intended to cover various alternatives, modifications, and equivalents, as will be appreciated by those of skill in the art.

Various embodiments of the present disclosure provide for the detection of mercury vapor using a temperature-stabilized film. In accordance with various embodiments, apparatus of the present disclosure can comprise, for example, mercury detectors configured to determine whether mercury is present in a sample. In various embodiments, for example, the mercury detector includes a mercury-sensitive surface. The mercury-sensitive surface can comprise, for example, a surface of a substrate comprising a plurality of gold nanoparticles disposed thereon.

By "nanoparticles" is meant particles that have an average size in the nanometer size range, such as an average size ranging from 1 nm to 1000 nm. By "average size" is meant the statistical mean average size. For example, nanoparticles of the present disclosure may have an average size ranging from 1 nm to 1000 nm, including from 1 nm to 750 nm, or from 1 nm to 500 nm, or from 1 nm to 250 nm, or from 1 nm to 100 nm, such as from 10 nm to 75 nm. In some instances, the nanoparticles may have a smaller average size ranging from 1 nm to 100 nm, or 1 nm to 75 nm, such as from 1 nm to 50 nm, including from 1 nm to 25 nm, or from 1 nm to 10 nm, or from 1 nm to 5 nm, or from 3 nm to 5 nm.

In certain embodiments, the nanoparticles are arranged on a surface of the substrate in one or more layers of nanoparticles. In some embodiments, the nanoparticles are arranged in a single layer on the surface of the substrate. A single layer can be, for example, a layer that is one-particle thick. For example, the nanoparticles can be arranged in a monolayer on the surface of the substrate. By "monolayer" is meant a single, closely packed layer of nanoparticles on the surface of the substrate. In some cases, the monolayer is substantially continuous, such that there are substantially no gaps between adjacent nanoparticles. For example, nanoparticles in a monolayer may be in contact with surrounding adjacent nanoparticles.

In a variety of embodiments, the nanoparticles are arranged in a submonolayer on the surface of the substrate. By "submonolayer" is meant a layer of nanoparticles on the surface of the substrate, where the layer is discontinuous in one or more regions. For example, nanoparticles in a submonolayer can be dispersed such that the nanoparticles do not substantially contact surrounding nanoparticles. In some embodiments, a submonolayer can include one or more groupings (e.g., islands) of nanoparticles surrounded by one or more regions of the substrate surface. In some embodiments, the groupings of nanoparticles can be dispersed such that the groupings of nanoparticles do not substantially contact surrounding groupings of nanoparticles. In other embodiments, the groupings of nanoparticles can be interconnected by one or more bridges of nanoparticles to form a substantially contiguous submonolayer on the surface of the substrate.

In accordance with various embodiments, a layer of nanoparticles on a substrate surface comprises a density of $10\times10^{12}$ nanoparticles/cm$^2$ or less, such as $9\times10^{12}$ nanoparticles/cm$^2$ or less, or $8\times10^{12}$ nanoparticles/cm$^2$ or less, or $7\times10^{12}$ nanoparticles/cm$^2$ or less, including $6\times10^{12}$ nanoparticles/cm$^2$ or less, or $5\times10^{12}$ nanoparticles/cm$^2$ or less, or $4\times10^{12}$ nanoparticles/cm$^2$ or less, or $3\times10^{12}$ nanoparticles/cm$^2$ or less, or $2\times10^{12}$ nanoparticles/cm$^2$ or less, or $1\times10^{12}$ nanoparticles/cm$^2$ or less, or $9\times10^{11}$ nanoparticles/cm$^2$ or less, or $8\times10^{11}$ nanoparticles/cm$^2$ or less, or $7\times10^{11}$ nanoparticles/cm$^2$ or less, or $6\times10^{11}$ nanoparticles/cm$^2$ or less, or $5\times10^{11}$ nanoparticles/cm$^2$ or less, or $4\times10^{11}$ nanoparticles/cm$^2$ or less, or $3\times10^{11}$ nanoparticles/cm$^2$ or less, or $2\times10^{11}$ nanoparticles/cm$^2$ or less, or $1\times10^{11}$ nanoparticles/cm$^2$ or less.

In various embodiments, nanoparticles of a mercury detector are comprised of a material that adsorbs mercury. For instance, the nanoparticles can comprise a material, such as a metal. In some cases, the metal is a metal that adsorbs mercury. For example, the metal can be a metal capable of adsorbing mercury from a surrounding sample fluid, such as mercury vapor in a gaseous sample, or mercury in a liquid sample. In some embodiments, the metal comprises gold. As such, in some embodiments, a mercury sensor can include gold nanoparticles disposed on a surface of the substrate. The gold nanoparticles can be arranged, for example, in a monolayer or a submonolayer on the surface of the substrate.

In a variety of embodiments, the nanoparticles comprise a shape that is substantially symmetrical. For example, in various embodiments, the nanoparticles can be substantially spherical. By substantially spherical is meant that the nanoparticles have a three-dimensional shape that defines or substantially approximates a sphere. In some instances, the spherical nanoparticles have an average diameter ranging from 1 nm to 100 nm, or 1 nm to 75 nm, such as from 1 nm to 50 nm, including from 1 nm to 25 nm, or from 1 nm to 10 nm, or from 1 nm to 5 nm, or from 3 nm to 5 nm. In certain embodiments, the spherical nanoparticles have an average diameter ranging from 3 nm to 5 nm. By "average diameter" is meant the statistical mean average diameter. In some cases, the spherical nanoparticles have a surface area to volume ratio of 0.1 or more, such as 0.2 or more, including 0.3 or more, or 0.4 or more, or 0.5 or more, or 0.6 or more, or 0.7 or more, or 0.8 or more, or 0.9 or more, or 1.0 or more, or 1.2 or more, or 1.4 or more, or 1.6 or more, or 1.8 or more, or 2 or more, or 2.5 or more, or 3 or more, or 3.5 or more, or 4 or more, or 4.5 or more, or 5 or more.

In certain embodiments, the nanoparticles comprise an elongated shape. For example, a nanoparticle for use herein can comprise a length that is longer than its width. For instance, an elongated nanoparticle may have an aspect ratio, which is the ratio of the length of the nanoparticle to the width of the nanoparticle. In certain embodiments, the elongated nanoparticle has an aspect ratio greater than 1, such as 1.5 or more, including 2 or more, or 2.5 or more, or 3 or more, or 3.5 or more, or 4 or more, or 4.5 or more, or 5 or more, or 6 or more, or 7 or more, or 8 or more, or 9 or more, or 10 or more. For example, the elongated nanoparticle may have an aspect ratio of 2 or more. In certain embodiments, the elongated nanoparticle has an aspect ratio ranging from 1 to 10, such as from 1 to 7, including from 1 to 5, or from 2 to 5, or from 2.5 to 4.5.

In some embodiments, an elongated nanoparticle for use herein comprises a length ranging from 1 nm to 1000 nm, including from 1 nm to 750 nm, or from 1 nm to 500 nm, or from 1 nm to 250 nm, or from 1 nm to 100 nm, such as from 10 nm to 75 nm, or from 25 nm to 75 nm, or from 50 nm to 75 nm. For instance, the elongated nanoparticle may have a length ranging from 50 nm to 75 nm, such as a length of 60 nm. In some embodiments, the elongated nanoparticle has a width ranging from 1 nm to 1000 mu, including from 1 nm to 750 nm, or from 1 nm to 500 nm, or from 1 nm to 250 nm, or from 1 nm to 100 nm, such as from 10 nm to 75 nm, or from 10 nm to 50 nm. For instance, the elongated nanoparticle may have a length ranging from 10 nm to 50 nm, such as a width of 20 nm.

In some embodiments, an elongated nanoparticle for use herein comprises a surface-area-to-volume ratio of 0.1 or more, such as 0.2 or more, including 0.3 or more, or 0.4 or more, or 0.5 or more, or 0.6 or more, or 0.7 or more, or 0.8 or more, or 0.9 or more, or 1.0 or more, or 1.2 or more, or 1.4 or more, or 1.6 or more, or 1.8 or more, or 2 or more, or 2.5 or more, or 3 or more, or 3.5 or more, or 4 or more, or 4.5 or more, or 5 or more. For example, the elongated nanoparticle may have a surface area to volume ratio of 0.2 or more. In some instances, the elongated nanoparticle has a surface are to volume ratio ranging from 0.1 to 3, such as from 0.1 to 2, including from 0.1 to 1, or from 0.1 to 0.5, or from 0.1 to 0.4, or from 0.1 to 0.3, or from 0.2 to 0.3.

In some embodiments, an elongated nanoparticle for use herein comprises an elongated shape, such as, but not limited to, a cylinder (e.g., a nanocylinder) or a rod (e.g., a nanorod). In some embodiments, the elongated nanoparticle has a cross-sectional profile (e.g., a cross section that intersects the longitudinal axis of the elongated nanoparticle) that has a shape that is substantially circular. It is noted that other cross-sectional profiles can be employed, such as, but not limited to, an elongated nanoparticle comprising a cross-sectional profile in the shape of an ellipse, a rectangle, a square, an oval, an irregular shape, and the like.

In accordance with various embodiments, nanoparticles for use herein are substantially free of a surface coating. Nanoparticles that are substantially free of a surface coating can be configured such that an exterior surface of each nanoparticle is directly exposed to the surrounding environment. For example, during fabrication of the mercury sensor, the nanoparticles can be washed to remove any surface coating present on the nanoparticles. The surface coating can be removed before or after the nanoparticles are disposed upon a surface of a substrate of the mercury detector. In some embodiments, exterior surfaces of the nanoparticles that are exposed to the surrounding environment (including a sample to be tested for the presence of mercury) are substantially free of a surface coating.

According to various embodiments, a plurality of nanoparticles are disposed upon a surface of a substrate. In various embodiments, the nanoparticles can be attached to a surface of the substrate, such as a major substantially planar surface. In some embodiments, such attachment can be, for example, via covalent bonds or non-covalent interactions, such as, but not limited to, ionic bonds, hydrophobic interactions, hydrogen bonds, van der Waals forces (e.g., London dispersion forces), dipole-dipole interactions, and the like.

In some embodiments, nanoparticles are disposed upon a substantially planar surface of a substrate. In various embodiments, an opposing side of the substrate is substantially free of nanoparticles, such that only one surface of the substrate has nanoparticles disposed thereon. In some embodiments, an optical fiber is used as the substrate and a plurality of nanoparticles are disposed upon to an exterior surface of the optical fiber. For example, the nanoparticles can be attached to a portion of an elongate optical fiber where the exterior surface is exposed (e.g., substantially free of surface coatings). In various embodiments, such portion of an optical fiber comprises an end region thereof.

In accordance with various embodiments, a substrate for use herein comprises a substantially transparent material such that light can pass through the substrate. In some embodiments, the substrate is substantially planar. In certain embodiments, a substantially planar surface of a substrate of a mercury sensor comprises an area of 10 cm$^2$ or less, such as 5 cm$^2$ or less, including 3 cm$^2$ or less, or 1 cm$^2$ or less, including 50 mm$^2$ or less, or 20 mm$^2$ or less, such as 10 mm$^2$ or less, or 5 mm$^2$ or less, or even smaller. For example, the mercury sensor substrate can comprise dimensions in the range of 10 μm×10 μm to 10 mm×10 mm, including dimensions of 10 mm×10 mm or less, such as 5 mm×5 mm or less, for instance 1 mm×l mm or less, or 100 μm×100 μm or less, or 50 μm×50 μm or less. In various embodiments, the substrate is comprised of a transparent material, such as, but not limited to, glass (e.g., silica glass), quartz, and the like. In certain embodiments, the substrate includes a mirror backing.

In certain embodiments, the substrate comprises an optical fiber (i.e., a fiber optic cable). The optical fiber can have a diameter of, for example, 1 mm or less, such as 750 μm or less, including 500 μm or less, or 250 μm or less, or 100 μm or less, or 50 μm or less, or 25 μm or less, or 10 μm or less or 5 μm or less. In some embodiments, the optical fiber has a diameter of 750 μm or less, such as a diameter of 600 μm. In some embodiments, the optical fiber comprises a transparent material, such as, but not limited to, glass (e.g., silica glass), and the like.

In accordance with various embodiments, a mercury detector of the present teachings includes a flow cell. The flow cell can be configured, for example, to carry or direct a flow of a fluidic sample (e.g., gaseous or liquid) through the mercury detector. For example, the flow cell can be configured to carry a flow of a gas (e.g., a gaseous sample or a conditioning gas) through the mercury detector. In some embodiments, the flow cell can be configured to carry or direct a flow of a sample fluid through the mercury detector. In various embodiments, a substrate surface supporting a plurality of nanoparticles can contact a flow of fluid (e.g., gas or liquid) directed or passed through the system. For example, in various embodiments, such surface can comprise an interior-facing surface of the flow cell. In some embodiments, the flow cell is configured such that the fluid flows across (e.g., substantially parallel to) the surface of the mercury sensor as the fluid flows through the flow cell.

In various embodiments, the system includes a gas source in fluidic communication with the flow cell. The gas source can be configured, for example, to provide a flow of a gas through the flow cell. The gas can be, for example, a gaseous sample to be tested for the presence of mercury, such as a gaseous sample suspected of containing mercury. In various embodiments, the gas source provides a conditioning gas, such as mercury-free air, useful for preconditioning nanoparticles of a film disposed on a surface region of a transparent substrate prior to sample testing.

In other embodiments, the flow cell can be configured such that a flow of incoming gas is substantially perpendicular to a substantially planar surface of the mercury sensor. For instance, the flow cell can include a nozzle arranged substantially perpendicular to the surface of the mercury sensor. Gas from the gas source can flow through the nozzle and contact the mercury sensor substantially perpendicularly to the surface of the mercury sensor. In some embodiments, this perpendicular configuration can facilitate an increase in the sensitivity of the mercury detector.

In accordance with various embodiments, a mercury detector of the present teachings includes a light source. The light source can be configured, for example, to direct light from the light source to the mercury sensor. For example, the light source can be configured to direct light from the light source to a transparent substrate of the mercury sensor. As described above, the transparent substrate can comprise one surface with nanoparticles attached and an opposing surface can be substantially free of nanoparticles. In such embodiments, the light source can be configured, for example, to direct light from the light source to a side of the transparent substrate opposite the side of the substrate with the nanoparticles. Stated another way, the light source can be configured to direct light from the light source to the side of the transparent substrate that is substantially free of nanoparticles.

In certain embodiments, the light source is configured to direct light to the mercury-sensitive surface at an angle. The angle can be measured as the angle between the incident light and a line perpendicular to the surface of the substrate. In some instances, the angle is from 0 to 90 degrees, such as from 15 to 75 degrees, including from 30 to 60 degrees.

In certain embodiments, the light source comprises a visible light source. The visible light source can be configured, for example, to emit light in the visible range of the electromagnetic spectrum. According to various embodiments, the light source can be configured, for example, to emit light in the ultraviolet (UV) range or the infrared range of the spectrum. In embodiments of the light source configured to emit light in the visible range of the spectrum, the light source can comprise, but is not limited to, a lamp (e.g., a halogen lamp), a laser, a light emitting diode (LED), and the like. The visible light source can be configured, for example, to operate at an actively controlled and stable temperature. The visible light source can be configured, for example, with a bandpass filter. In various embodiments, a bandpass filter is employed comprising a full width half maximum (FWHM) of 10 nm of transmitted wavelengths.

In accordance with various embodiments, the mercury detection system includes a light detector. In some embodiments, a light detector can be configured, for example, to detect light emitted from the mercury sensor in the visible range of the electromagnetic spectrum. In some embodiments, the detector is configured to detect light emitted from the mercury-sensitive surface in the ultraviolet range of the electromagnetic spectrum. In some embodiments, the detector is configured, for example, to detect light emitted from the mercury-sensitive surface in the infrared range of the electromagnetic spectrum. In some cases, the detector is configured, for example, to detect light emitted from the mercury-sensitive surface in more than one range of the electromagnetic spectrum, such as in the UV and visible, or the visible and infrared, or the UV, visible and infrared ranges of the spectrum. In certain embodiments, the detector comprises a light detector, such as, but not limited to a silicon photodiode, a UV-Vis photodetector, a spectrometer, and the like.

According to various embodiments, the light detector can be configured, for example, to detect emissions and/or reflected light from the mercury-sensitive surface, such as electromagnetic emissions from the mercury-sensitive surface and/or light from the light source reflected at the mercury-sensitive surface. For example, the detector can be configured to detect light from the light source reflected at the mercury-sensitive surface. In some embodiments, the system is configured, for example, to detect a minimum in the light reflected at the mercury-sensitive surface. Stated another way, the system can be configured to detect a maximum in the absorbance (e.g., a local maximum in the absorbance). In some embodiments, the system is configured, for example, to detect a wavelength at which a maximum in absorbance occurs (i.e., a peak localized surface plasmon resonance (LSPR) wavelength). In some embodiments, the system is configured, for example, to detect changes in absorbance in single active band of the spectrum.

In accordance with various embodiments, the mercury detector is configured to determine whether mercury is present is a sample based on the localized surface plasmon resonance (LSPR) wavelength of the nanoparticles. For example, the system may be configured to detect a peak LSPR wavelength (e.g., the LSPR wavelength at which a local maximum in absorbance occurs). In some embodiments, the peak LSPR wavelength can provide a qualitative indication of whether mercury is present or absent in a sample. For instance, the system may be configured to detect a shift or a change in the peak LSPR wavelength (e.g., as compared to a baseline or control measurement in the absence of mercury). In some embodiments, a shift in the peak LSPR wavelength provides an indication of the presence of mercury in the sample. Without being limited to any particular theory, as a sample containing mercury contacts the mercury-sensitive surface, mercury from the sample may be adsorbed onto the nanoparticles (e.g., gold nanoparticles). The adsorption of mercury onto the nanoparticles can cause the peak LSPR wavelength to shift from its original wavelength (e.g., the peak LSPR wavelength in the absence of mercury). As such, a shift in the peak LSPR wavelength can indicate the presence of mercury in the sample. According to various embodiments, a shift in the peak LSPR wavelength proportional to the mass fraction of mercury adsorbed by the nanoparticles provides a means for quantification of mercury concentration in the sample.

In certain embodiments, the sensitivity of the system depends on the surface area to volume (SA:V) ratio of the nanoparticles. For example, the shift in the peak LSPR wavelength may depend on the SA:V ratio of the nanoparticles. In some embodiments, an increase in the SAN ratio of the nanoparticles increases the magnitude of the shift in the peak LSPR wavelength for a given concentration of mercury in a sample.

In certain embodiments, the system is configured to detect mercury vapor at a concentration of 18 mg/m³ or less. For example, the system can be configured to detect mercury vapor at a concentration of (e.g., the system may be configured to have a limit of detection of) 100 µg/m³ or less, such as 75 µg/m³ or less, including 50 µg/m³ or less, or 25 µg/m³ or less, or 10 µg/m³ or less, or 5 µg/m³ or less, or 1 µg/m³ or less, or 750 ng/m³ or less, or 500 ng/m³ or less, or 250 ng/m³ or less, or 100 ng/m³ or less, or 75 ng/m³ or less, or 50 ng/m³ or less, or 25 ng/m³ or less, or 10 ng/m³ or less, or 5 ng/m³ or less, or 1 ng/m³ or less. In certain embodiments, wherein the system is configured to have a low limit of detection as described above, the system can detect mercury in samples where the sample is directly analyzed by the system. For example, the sample can be obtained and analyzed by the system directly with no preconditioning (e.g., concentration) or advance preparation of the sample prior to analysis.

In various embodiments, the system further comprises a temperature controller or control unit. In various embodiments, a temperature control unit comprises a heat source. The heat source can be configured, for example, to facilitate temperature control of the mercury sensor. For example, the heat source can be configured to heat the mercury sensor. In some embodiments, for example, the heat source comprises, but is not limited to, a polyimide film heater, a heating coil, a heating lamp, a Peltier device, and the like. In some embodiments, for example, the heat source is configured to heat the mercury sensor to a temperature of 30° C. or more, such as 40° C. or more, or 50° C. or more, or 60° C. or more, or 70° C. or more, or 80° C. or more, or 90° C. or more, or 100° C. or more, or 110° C. or more, or 120° C. or more, or 130° C. or more, or 140° C. or more, or 150° C. or more, or 160° C., or more, or 170° C. or more, or 200° C. or more. In some cases, the heat source is configured to heat the mercury sensor to a temperature ranging from 100° C. to 200° C., such as from 100° C. to 190° C., including from 100° C. to 180° C., or from 110° C. to 170° C., or from 120° C. to 160° C. In various embodiments, the temperature control unit is configured to heat a mercury-sensitive film supported on a transparent substrate to a selected temperature and to maintain such temperature substantially constant for a desired period of time (e.g., throughout a period of sample testing.)

Next, various embodiments of the disclosure are described with reference to the appended drawings.

FIG. 1 is a functional block diagram of a mercury detector in accordance with various embodiments of the present teachings. In FIG. 1, a subsystem, indicated at 1, includes a flow cell containing an LSPR film comprising gold or gold-mercury amalgam nanoparticles, which is the active transducer turning a mercury vapor concentration present in the flow cell into an optical response. A temperature measurement of the film, indicated at 2, effected via a K-type thermocouple, is transmitted to a temperature-control subsystem, indicated at 3. The temperature-control subsystem 3 compares the film temperature to a set point (for example, 30° C. or more, 40° C. or more, 50° C. or more, 60° C. or more, 70° C. or more, 80° C. or more, 90° C. or more, 100° C. or more, 110° C. or more, 120° C. or more, 130° C. or more, 140° C. or more, 150° C. or more, 160° C., or more, 170° C. or more, or 200° C. or more) and applies a control algorithm to determine a quantity of electricity to send to a resistive heating element, denoted as 12 in FIG. 2. This quantized electrical current at 24V is sent back to subsystem 1 via element 4 (FIG. 1).

An inlet and an outlet, indicated at 5 and 6 in FIG. 1, respectively, direct a continuous stream of mercury vapor in a gas stream (e.g., at 0.1 L/min or more, IL/min or more, or 5 L/min or more). An optical signal originating at a broad-spectrum LED source is introduced to subsystem 1 via a fiber optic cable, indicated at 7 in FIG. 1. The optical signal, modified by the absorbance of the film, is transmitted out of the flow cell via a second fiber optic cable, indicated at 8 in FIG. 1. This optical signal from the second fiber optic cable 8 is then converted into a digital signal by a signal processing and analysis subsystem, indicated at 9. This digital signal can be compared to a stored calibration by the signal processing and analysis subsystem 9 in order to provide the mercury concentration in the flow stream.

Figure 2:
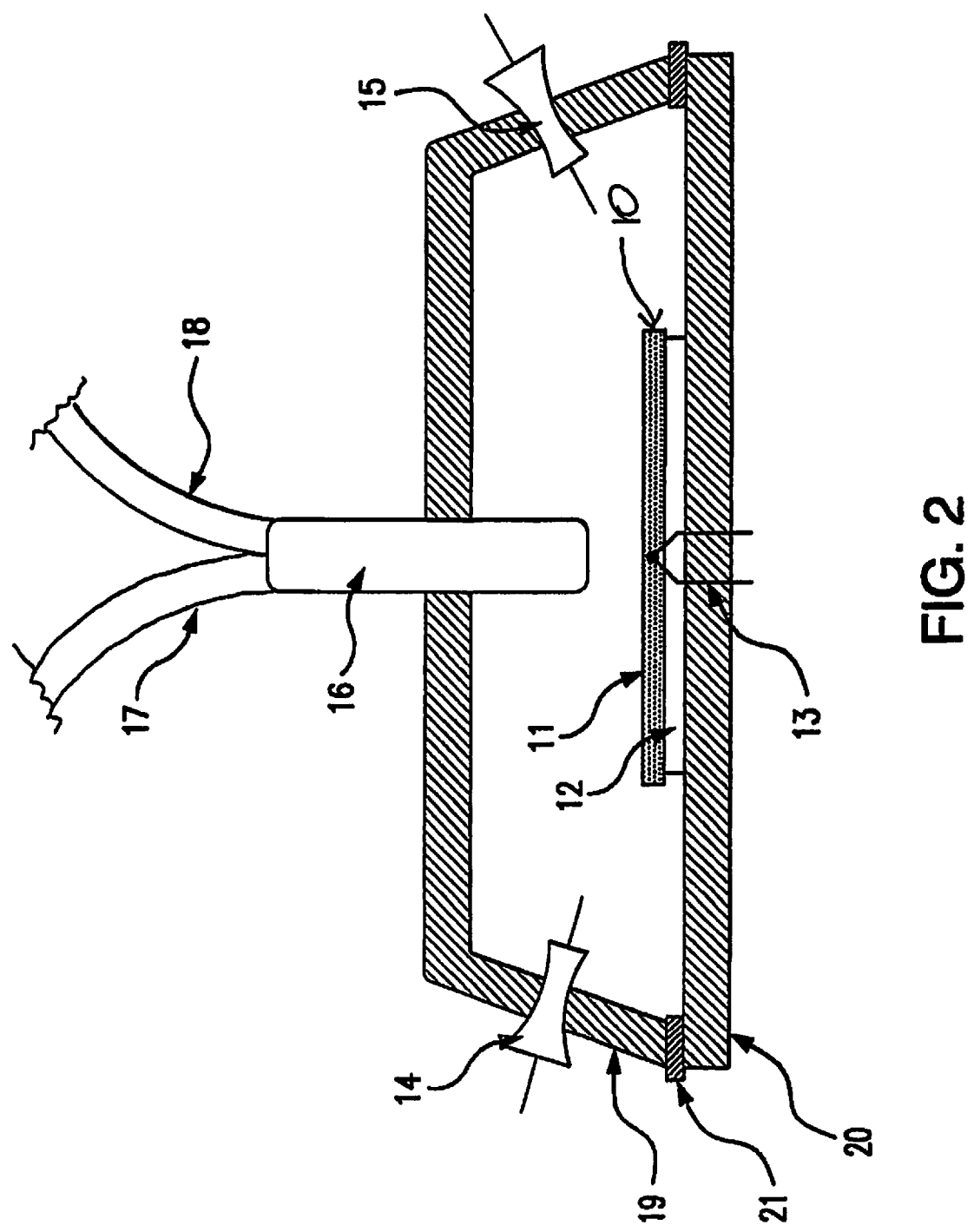
FIG. 2 schematically depicts an LSPR mercury detector, according to various embodiments of the present disclosure.

FIG. 2 is a cross sectional schematic of the detector system, centered on the flow cell. In FIG. 2, a gold nanoparticle LSPR film, denoted at 11, is supported on a mirrored transparent substrate 10. A resistive-film heater, denoted at 12, applies heat (e.g., at 1 W or more, 5 W or more, or 10 W or more) to maintain the temperature set point of film. A thermocouple, denoted at 13, can measure the film temperature. Inlet and outlet nozzles, denoted at 14 and 15, respectively, allow a sample gas to flow through the flow cell. A reflection probe, denoted at 16, directs visible light from a light source, such as an LED light source, via a fiber-optic cable, denoted at 17, and then collects the light reflected and modified by the LSPR film 11 to the signal processing subsystem 9 (FIG. 1) via a second fiber optic cable, denoted at 18.

A hermetic vessel is defined by a flow cell top, at 19, a flow cell base, at 20, and a gasket material, at 21, to seal the flow cell. The hermetic vessel can contain the mercury-vapor-containing gas stream over the transducing LSPR film 11.

Aspects of various embodiments of the present disclosure include methods for determining whether mercury is present is a sample. Such methods can include, for example, contacting a sample to a mercury-sensitive surface of a mercury detection system to produce a sample-contacted mercury sensor. In some embodiments, the contacting includes directing a flow of a fluidic sample to contact the mercury sensor. For gaseous samples, directing the flow of a sample can include directing the gaseous sample through a flow cell to contact a mercury-sensitive surface within the flow cell. The gas can be a gaseous sample to be tested for the presence of mercury, such as a gaseous sample suspected of containing mercury. The flow of the gaseous sample can be directed to contact the surface of the mercury sensor that has the nanoparticles, such as gold-mercury amalgam nanoparticles, supported thereon. In some embodiments, the directing includes directing the flow of the sample across (e.g., substantially parallel to) a major planar surface of the mercury sensor. In other embodiments, the directing includes directing the flow of the sample to the mercury sensor such that the flow of the sample is substantially perpendicular to a major planar surface of the mercury sensor.

In various embodiments, a method of the present disclosure can include directing light from a light source to the sample-contacted mercury-sensitive surface. In some embodiments, the light is directed to a surface of the mercury sensor opposite the surface of the mercury sensor that has gold-mercury amalgam nanoparticles supported thereon. For example, the mercury sensor can include a mirrored substrate with one surface that includes a layer (e.g., a submonolayer) of nanoparticles attached.

Various embodiments of the method can also include detecting light emitted and/or reflected from the mercury sensor. In some embodiments, for example, the method includes detecting changes in visible light absorption of the nanoparticles (e.g., gold or gold-mercury amalgam nanoparticles) to determine whether mercury is present in the sample. For example, the method can include detecting changes in the intensity of transmitted light in a band of the visible spectrum. This shift in the peak LSPR wavelength can provide an indication of the presence of mercury in the sample.

Figure 3:
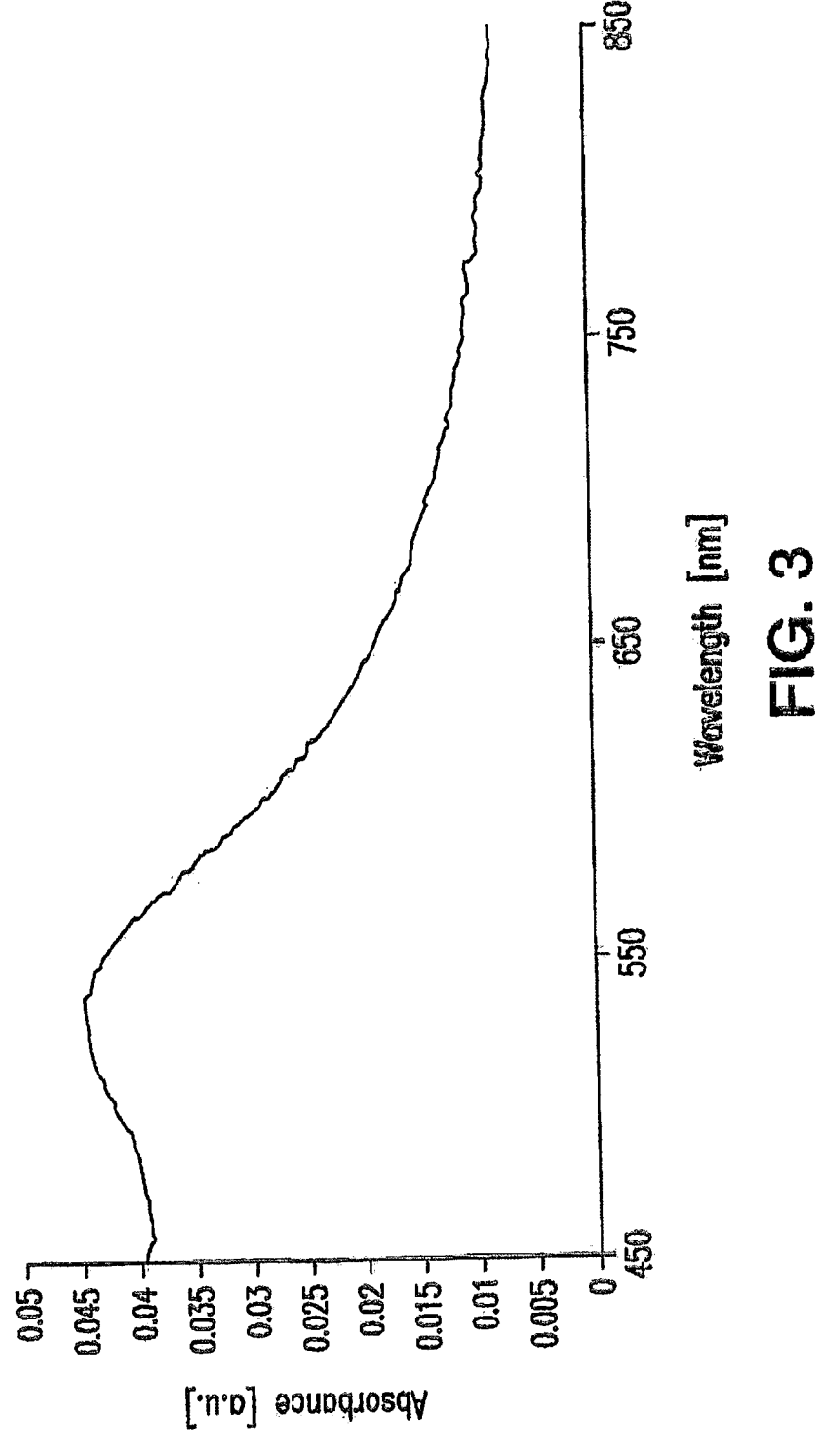
FIG. 3 is a UV-Vis absorbance spectrum of a gold nanoparticle film, according to various embodiments of the present disclosure.
Figure 4:
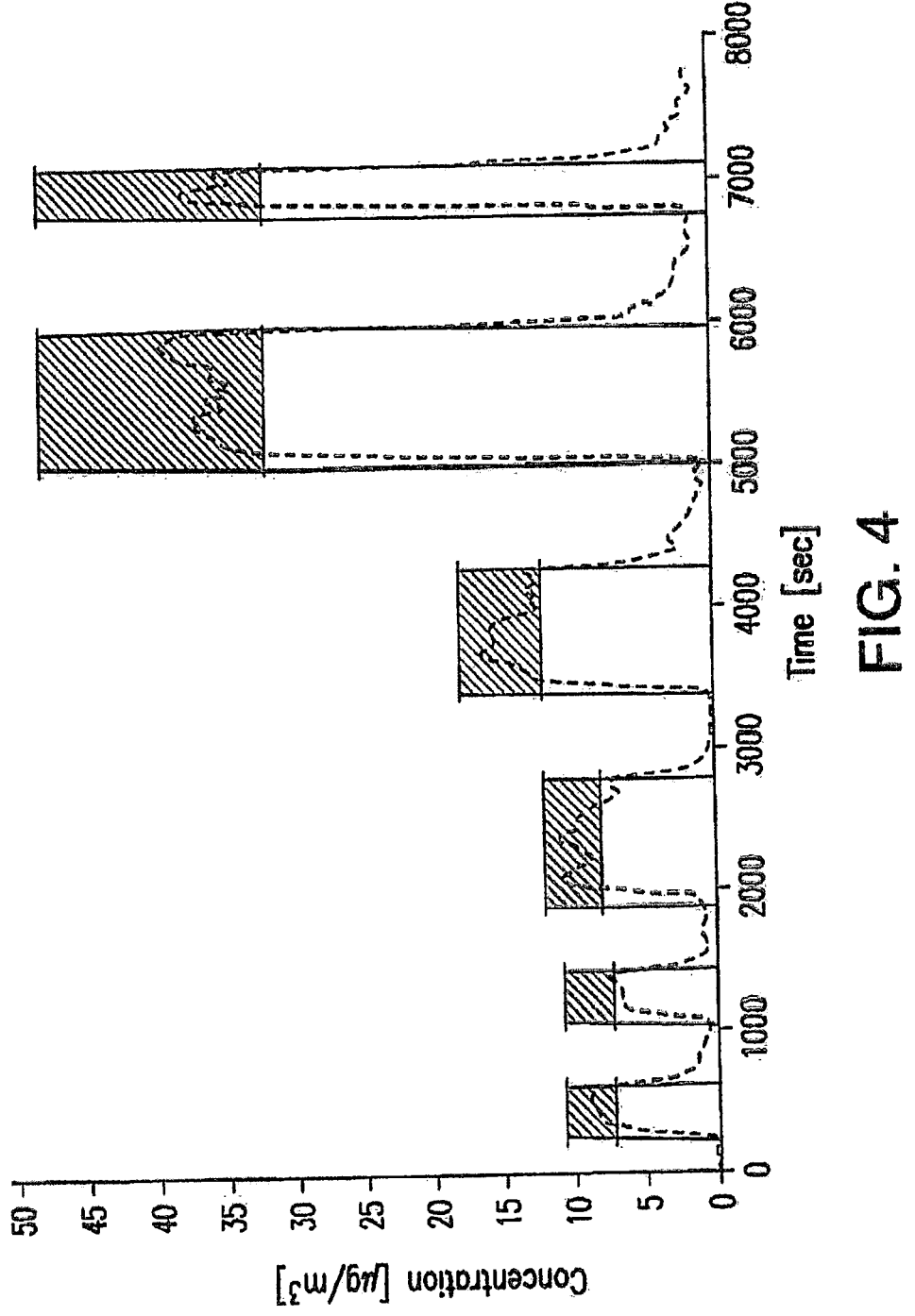
FIG. 4 is a concentration reading (dashed) using an equilibrium plasmonic detector at 80° C., with an overlay of calibration gas nominal concentration (black) w/uncertainty, according to various embodiments of the present disclosure.

Various embodiments of the present disclosure employ a temperature-stabilized LSPR film for the detection of mercury. FIG. 3 provides a graph of the intensity of a narrow band of visible light affected by the LSPR of the film as mercury is introduced to the flow cell containing that film. In some embodiments, a single band of light 10 nm wide is centered at a selected light frequency, such as 450 nm or higher, 460 nm or higher, 470 nm or higher, 480 nm or higher, 490 nm or higher, 500 nm or higher, 510 nm or higher, 520 nm or higher, 530 nm or higher, 540 nm or higher, or 550 nm or higher. The film is maintained at a temperature set point throughout a run, while a known quantity of mercury vapor is provided by a calibrated mercury vapor generation source. In some embodiments, the carrier gas comprises air. In various embodiments, a valve, upstream of the flow cell allows the mercury vapor to be introduced to the air stream, or not, in which case the air stream continues with no mercury. An exemplary recording of the response of the detector to mercury vapor is depicted in FIG. 4.

In accordance with various embodiments, a method of the present teachings can further include a step of quantifying the amount of mercury in a sample. For example, the quantifying can include determining the amount of mercury in the sample based on a shift in the localized surface plasmon resonance wavelength of the nanoparticles. By determining the shift in the peak LSPR wavelength based on the detected light, the concentration of mercury in the sample may be determined. In some embodiments, the LSPR peak shift is detected using a band of filtered visible light and one or more photodiodes.

Temperature-stabilized gold nanoparticle films of the present teachings can find application, for example, in the detection of mercury. In accordance with various embodiments, the system is continuous, and thus finds applications, for example, in situations where real-time mercury monitoring, uninterrupted by cycling of the gold surface, is desired.

Mercury monitoring can find application, for example, in air, nitrogen, natural gas, or other matrices. It is noted that LSPR sensors can find application, for example, in targeting analytes in addition to or other than mercury, for example, via modification of the film surface with appropriate receptors, as will be appreciated by those skilled in the art.

In various embodiments, applications of metallic surfaces for analysis can comprise a process including a first step wherein mercury is adsorbed onto a moderate temperature gold surface and a second step wherein the metallic surface is heated to release the mercury as vapor. In various embodiments, gold surfaces are held at moderate temperatures (i.e., from ambient or near ambient to about 50° C.) in mercury collection applications. Moderate temperatures can provide for quantitative collection of mercury on gold surfaces. Atomic spectroscopy methods can provide for measuring low levels of mercury (sub-ppb). Heating the gold surface (>100° C.-700° C.) regenerates the surface by desorbing all or substantially all the mercury.

In various embodiments, the mercury-sensitive film temperature is steady state and operates continuously. At a given temperature, an amalgam nanoparticle film establishes an equilibrium surface concentration of mercury and corresponding shift in LSPR response. This differs from prior applications of gold surfaces in mercury analysis where regeneration is a required step. A temperature-stabilized film allows for effective measurement of relatively high levels of mercury vapor (~1 ppm-saturation). It will be appreciated that such high levels of mercury vapor would quickly saturate a moderate temperature gold film, rendering the sensor inaccurate.

Further aspects of the present teachings relate to methods and apparatus to increase the sensitivity of a plasmonic sensor.

According to various embodiments, an optical cavity is employed to increase the number of passes through a plasmonic film between a light source and a detector. In various embodiments, the plasmonic sensor works by measuring changes in extinction through the film. Increasing the number of passes through the film amplifies changes in extinction compared to a single pass optical path.

An optical cavity in accordance with various embodiments of the present teachings is an arrangement of mirrors such that the light coming from the source is reflected multiple times between the mirrors before reaching the detector. A variety of optical cavities have been developed for other optical applications. A typical application is to increase the pathlength of the beam within the cavity. According to the present teachings, on the other hand, the pathlength is not important, but rather the number of transits through the nanoscale film. In various embodiments, an optical cavity of the present teachings can have a very short beam path while still providing numerous passes through the film. A straightforward example is a parallel plane arrangement, two parallel mirrors. One, or both, of the inside faces of the mirrors can comprise an applied plasmonic film. The light enters and exits at opposite ends of the cavity (e.g., upstream and downstream, with respect to sample flow) and passes through the plasmonic film multiple times. In various embodiments, the free space or gap (aka, cavity) between mirrors can be used to introduce sample to the film. In various embodiments, the mirrors can be temperature controlled.

According to various embodiments, the film can comprise an array of metal nanomaterial, e.g., gold nanoparticles, that demonstrate localized surface plasmon resonance (LSPR). Changes in optical extinction of LSPR active nanoparticle films can be used to detect and quantify the adsorption of target analytes. For small changes in extinction the amplification is essentially proportional to transit count.

Among other things, a multi-pass plasmonic sensor according to the present teachings can be configured, for example, with features directed towards ease of use, portability, and/or other user-focused consideration(s). A sensor according to various embodiments, for example, can be configured for compactness, assembling convenience, and/or other generally desirable feature(s). Further, such a sensor can be adapted for amplifying the analyte signal (e.g., mercury signal). In various embodiments, a deposited nanoparticle film, such as described hereinabove, is disposed within an optical cavity defined by narrowly spaced, confronting mirrors. According to various embodiments, sample fluid (e.g., gas or liquid) can be passed through the cavity for optical interrogation. In this regard, a beam of light can be directed along a beam path such that it can enter and exit the cavity at near-normal incidence to the plane of the nanoparticle-coated mirror (e.g., within about five (5) degrees of normal).

Figure 7:
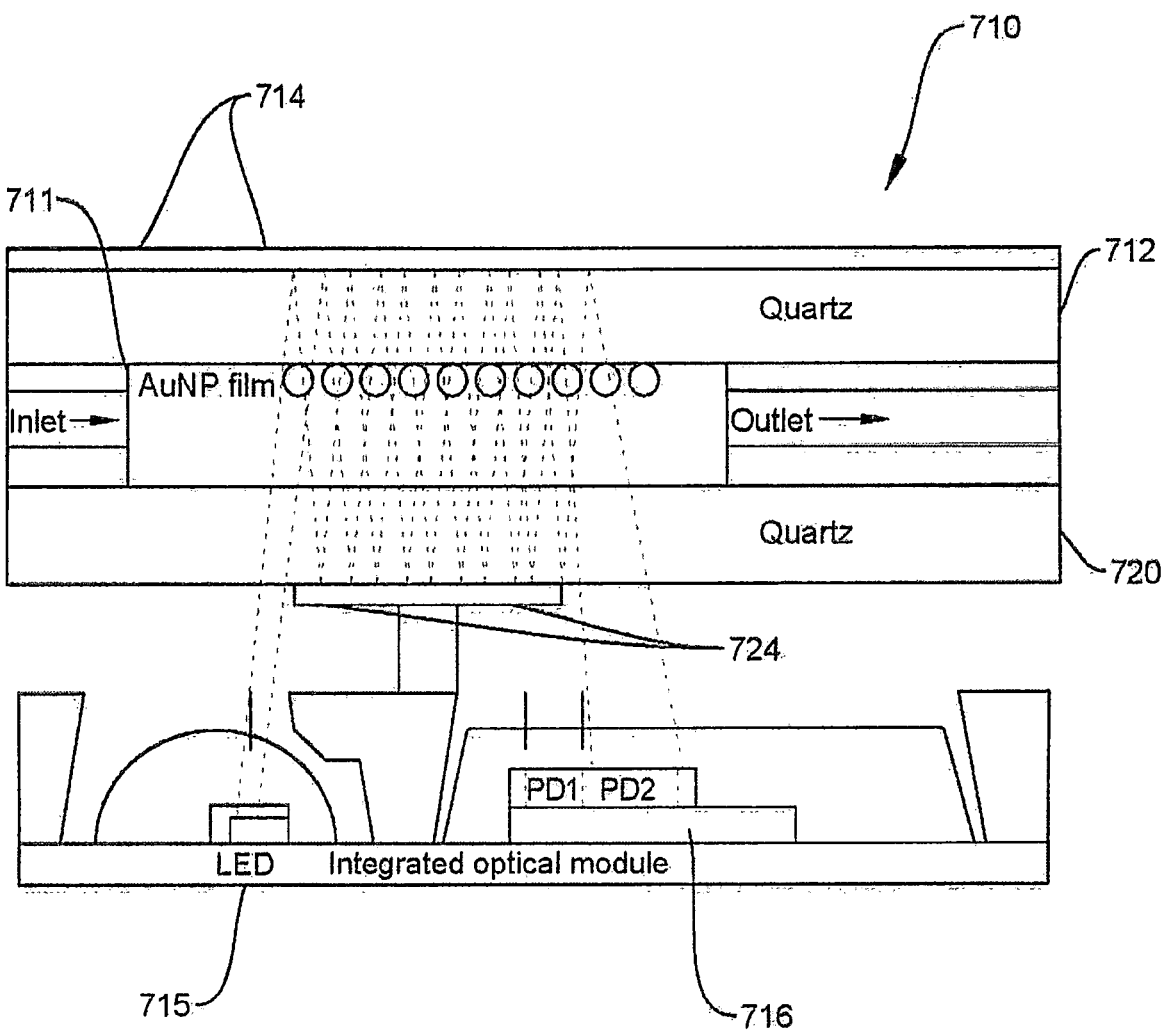

Further in these regards, and with reference now to the embodiment depicted in FIG. 7, a flow cell 710 can comprise a multi-pass plasmonic sensor, which multi-pass plasmonic sensor, in turn, can comprise, for example: a first substrate 712 comprising a first substantially planar, mirrored surface 714; and an analyte-sensitive film 711 disposed on a surface region of the first substrate 712, wherein the analyte-sensitive film 711 comprises a plurality of metallic nanoparticles having an affinity for a selected analyte of interest; and further, a second substrate 720 comprising a second substantially planar, mirrored surface 724, with a plane of the second mirrored surface 724 disposed in close fixed-spaced relation to, and substantially parallel with a plane of the first mirrored surface 714.

With continuing reference to FIG. 7, a light source 715 is configured for directing a substantially columnar beam of light along a beam path extending to the analyte-sensitive film. A light detector 716 is configured for detecting a localized surface plasmon resonance (LSPR) signal from the analyte-sensitive film. A temperature-control unit (not shown in FIG. 7) can maintain the analyte-sensitive film at a substantially constant selected temperature. In operation, the system can determine whether the analyte is present in a sample based on a LSPR signal detected from the analyte-sensitive film.

According to various embodiments, the first and second mirrored surfaces 714, 724 are configured to reflect a light beam entering the cavity between them, e.g., from just outside an outer edge of the first or the second mirrored surface, a predetermined number of times as the beam propagates, e.g., in a narrow zig-zag fashion, along a plane between the confronting mirrors, and ultimately exits the cavity in route to detector 716.

While conceptually similar to multi-pass gas spectroscopy, the active optical path length is no greater than the thickness of the plasmonic film (5 nm). According to various embodiments, about 20-30 film-passes can be performed within the dimensional and photonic specifications of the identified photonic front ends. In some embodiments, a multi-pass plasmonic sensor of the present teachings can provide, for example, about 20 times or greater as compared to a single pass plasmonic sensor.

EXAMPLES

The following examples are illustrative and not intended to limit the scope of the present disclosure or appended claims.

Example 1—Continuous Air Monitoring

Film Preparation and Characterization

Hydrophobic gold nanoparticles are suspended in chloroform and deposited onto the surface a quartz mirror using the Langmuir-Blodgett method. The resulting nanoparticle films is plasma cleaned in an oxygen plasma and characterized with a UV-Vis spectrometer. An exemplary absorbance spectrum is shown in FIG. 3. A portion of the quartz film is left substantially free of nanoparticles.

Continuous Mercury Vapor Generation

Mercury vapor in air is generated using mercury scrubbed, using activated carbon, compressed air and a mercury calibration source (PSA CavKit). The calibration source generates a flow (0-20 ml/min) of saturated mercury vapor from a temperature controlled (30-50° C.) supply of elemental mercury. The saturated mercury vapor is diluted in a flow (0-20 lpm) of clean air.

Detector

The above-described nanoparticle film on a quartz mirror substrate is mounted inside a flow cell composed of PEEK and Silconert® coated aluminum. Other features of the flow cell comprise: a gas inlet, a gas outlet, a heater (polyimide film heater), a thermocouple, and two fiber optic reflection probes. The cell is sealed with a Viton®, fluoroelastomer, O-ring to the face of the quartz mirror. Flow through the detector is pulled using a vacuum pump (Gast® 10D) with a flow of 2.5 lpm.

The temperature of the film is monitored and controlled using a pulse width modulated 24 VDC supply to the film heater.

The optical system includes a temperature-controlled light emitting diode (LED) with a bandpass filter (10 nm FWHM) coupled to the two fiber bundles of the reflection probes. The light is transmitted from the LED to two spots on the mirror (one with and one without nanoparticles), the reflected beams are collected, and final detection occurs at two silicon photodiodes. The photodiode signal is amplified, digitized, and recorded with custom electronics and software.

Experimental Procedure

The detector is turned on and allowed to stabilize temperatures of the LED and film. For these tests a film temperature of 80° C. is used. The detector is then connected to the calibration source and exposed to a range of controlled concentrations between zero and 40 µg/m$^3$. The photodiode signal is recorded for comparison in determining mercury vapor concentration.

Results

Upon exposure to mercury vapor there is an immediate shift in the photodiode signal. The shift stabilizes to a given value for a given concentration. Concentrations are reported every 0.35 seconds and are based on a quadratic calibration curve.

Example 2—Mercury Mass Determination with Direct Thermal Sample Treatment

A substantially similar technique is employed for measuring the mass of mercury in a soil or water sample. This example includes (ii) a sample thermal decomposition step and (ii) the mass is backed out of a calculation of an area under the concentration curve.

Figure 5:
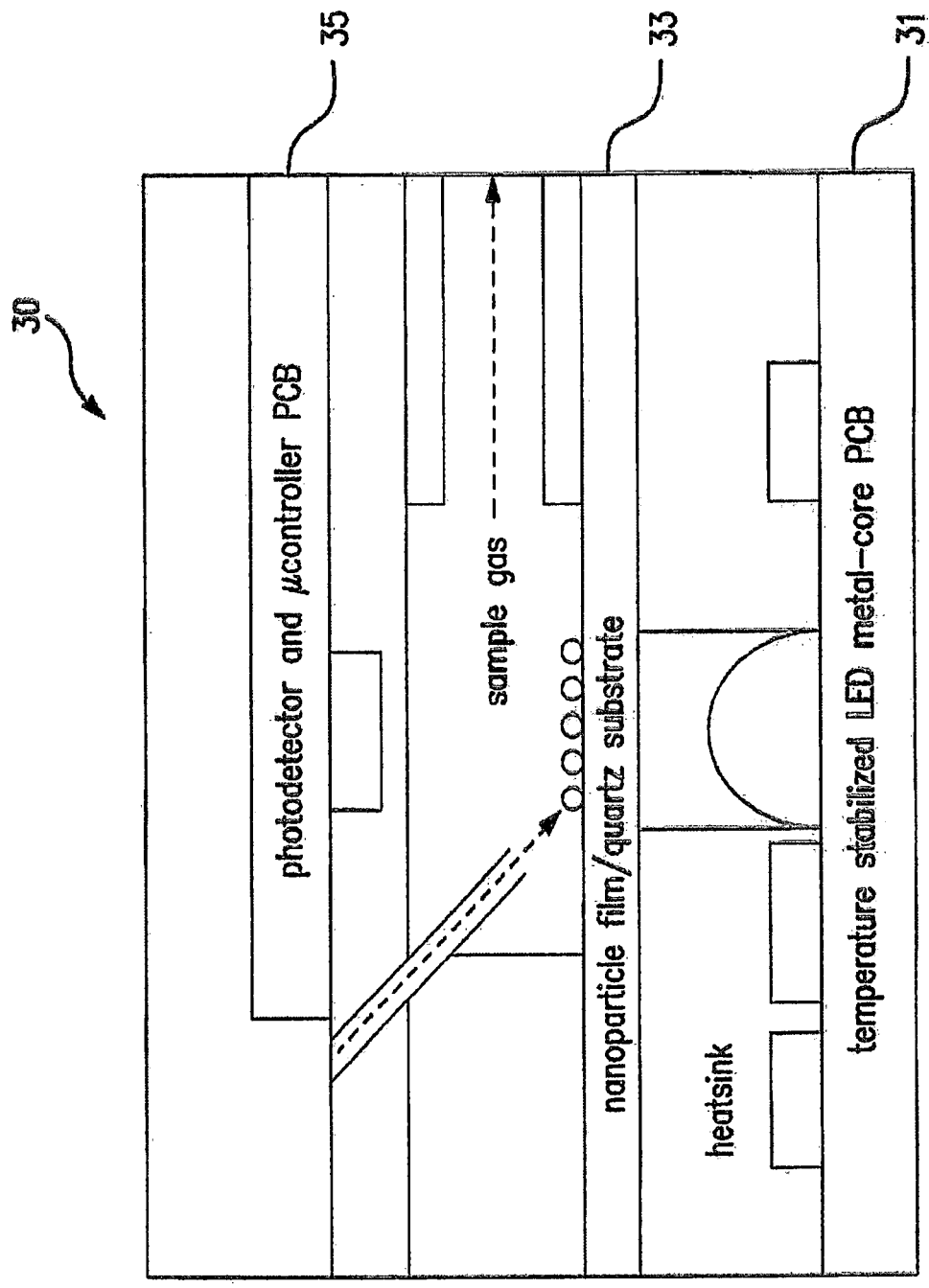
FIG. 5 schematically depicts a portable LSPR gas detector with combined temperature control of the LED and nanoparticle film, according to various embodiments of the present disclosure.

Example 3—a Portable LSPR Gas Detector with Combined Temperature Control of the LED and Nanoparticle Film With reference to FIG. 5, a gas-phase LSPR apparatus, indicated generally at 30, includes an LSPR film, optics, and a temperature controller. An LED light source 31, nanoparticle film/substrate 33, and photodetector board 35 are assembled into a sandwiched design. Separate modules of the detector are connected by optical fibers.

Two photodetectors, e.g., silicon photodiodes, monitor transmitted light through neighboring areas of the substrate—one with nanoparticles (signal) and one without (background). Apertures limit the probed area for each of the photodetectors. The emitted spectrum from a cyan LED light source is in the most dynamic band of the LSPR response. Temperature control of the plasmonic film and LED light source is unified.

At a given film temperature, changes in LSPR signal to mercury vapor concentrations are calibrated. The LSPR signal is monitored by following changes in transmission in a band of visible light (e.g., 520 nm, 10 nm FWHM). A non-linear but monotonic relationship is fit with a quadratic calibration curve.

FIG. 4 shows the performance of the described equilibrium apparatus/method at an 80° C. film temperature. Mercury vapor was generated in air using a PSA CavKit (a mercury calibration system based on a dilution of a stream of saturated mercury vapor from a temperature-controlled reservoir). During a 25 minutes test of mercury free air the equilibrium plasmonic detector demonstrated σ=0.045 µg/m$^3$.

A range of sensitivities is achieved by tuning the film temperature. Increasing the film temperature decreases the magnitude and increases the speed of the response.

Example 4—Pre-Conditioning of Mercury-Sensitive Film

A mercury-sensitive film comprising a plurality of gold-mercury amalgam nanoparticles is preconditioned as follows to substantially preclude irreversible mercury adsorption during use with a gaseous test sample at a substantially constant selected operating temperature:

(a) a gold-nanoparticle film is supported on a transparent substrate;

(b) the gold-nanoparticle film is heated to, and maintained at a substantially constant selected temperature, which temperature is that to be used subsequently in a method and apparatus for testing one or more samples for the presence of mercury;

(c) while maintaining the mercury-sensitive film at the substantially constant selected temperature:

(i) exposing the gold-nanoparticle film to mercury vapor in air while detecting for a first localized surface plasmon resonance (LSPR) signal from the mercury-sensitive film and allowing the first signal to stabilize; and then, (ii) exposing the gold-nanoparticle film to mercury-free air while detecting for a second LSPR signal from the mercury-sensitive film and allowing the second signal to stabilize.

Notes. Relatively high levels (>10 µg/scm typically) of mercury vapor can be used for time efficiency. Ensure that the temperature is stable through this process.

Example 5—Multi-Pass LSPR Sensor

According to various embodiments, an order of magnitude enhancement in sensitivity, or greater, can be achieved through the application of an optical technique of the present teachings referred to herein as "multi-pass plasmonic sensing."

In various embodiments, an optical cavity is utilized in connection with a two-dimensional array of nanoparticles, according to various embodiments of the present teachings, to increase the number of film transits. More particularly, a second mirror is provided, substantially parallel to the film mirror, to direct light from the LED back through the film multiple times before being measured at the other end of the cavity. Such plurality of film transits can amplify the relatively small changes in extinction due to analyte adsorption.

Such design is demonstrated experimentally, for example, by altering the optical cavity geometry. Narrowing the gap between the mirrors and lengthening the cavity in the direction parallel to the nanoparticle film can result in an increase in sensitivity that is in good agreement with the modelled number of film transits.

Exemplary results are shown in Table 1. Those skilled in the art will appreciate that increasing the sensitivity by a factor of 32 is a major accomplishment. Moreover, sensitivity is considered a primary specification of any sensor system and is a critical limit for many LSPR sensing applications.

TABLE 1

| Flow Cell Optics | Modeled # of Passes | Sensitivity [1/ng] | Normal-ized Sensi-tivity | Optical cavity length [mm] | Optical cavity gap [mm] |
|---|---|---|---|---|---|
| Traditional single mirror design | 2 | 1.56E−05 | 1.00 | N/A | N/A |
| Multipass #1 | 9 | 6.91E−05 | 4.43 | 1 | 1.5 |
| Multipass #1 with first surface mirror | 13 | 8.11E−05 | 5.20 | 1 | 1 |
| Multipass #2 | 38 | 2.60E−04 | 16.67 | 3.1 | 1 |
| Multipass #2 with first surface mirror | 75 | 5.00E−04 | 32.05 | 3.1 | 0.5 |

Sensitivity changes with number of passes through the plasmonic film.

According to various embodiments, increasing total film-transit count of the optical path can improve the signal strength. Without committing to any particular theory, the plasmonic film attenuates about 2% of the incident light within the active band with each transit. Thus, the attenuation (p) through the plasmonic film follows the function, $$\mu = 1 - 0.98^n$$

where n is the number of passes through the film.

Figure 6:
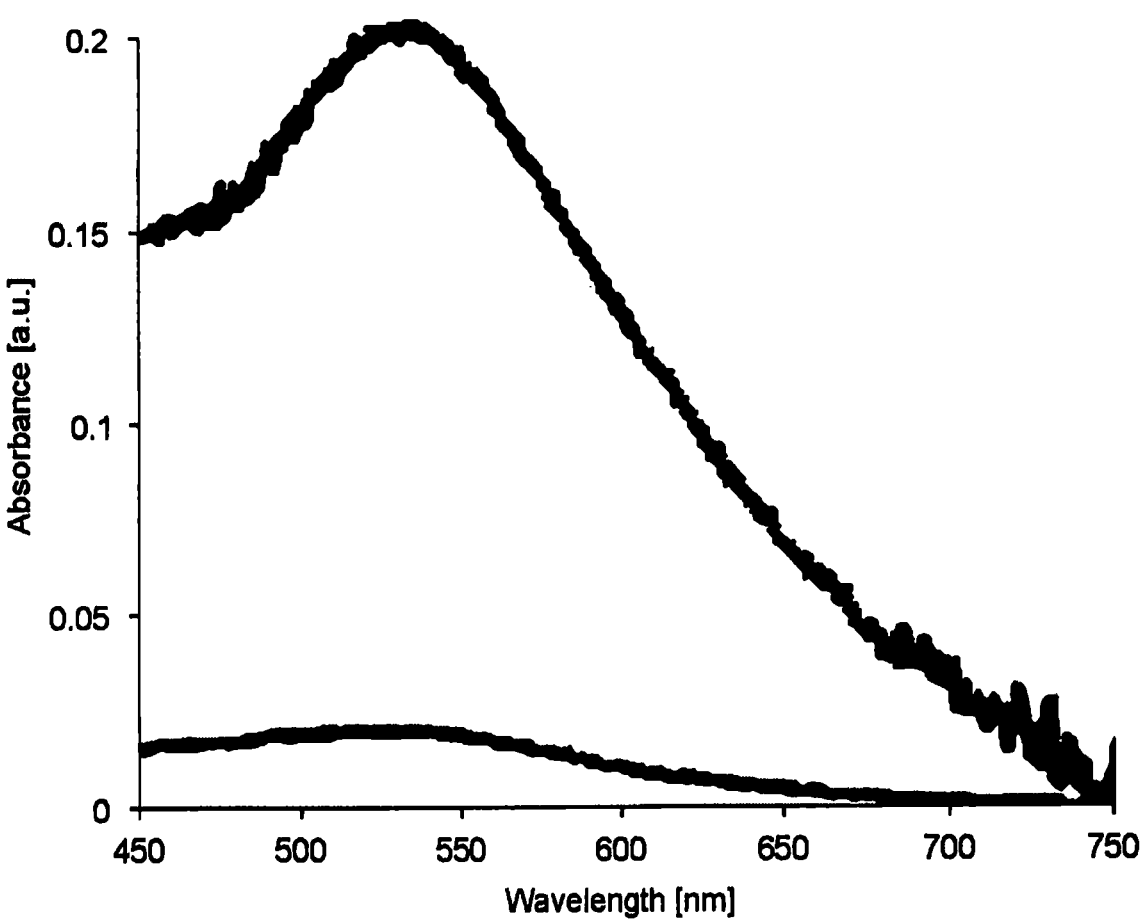
FIG. 6 graphically illustrates two absorbance measurements of the same film with different numbers of passes, according to various embodiments of the present disclosure; and, FIG. 7 schematically depicts a multi-pass plasmonic sensor, according to various embodiments of the present disclosure.

FIG. 6 shows first and second absorbance measurements of the same film with different numbers of passes. The plasmonic analyte signal is equivalently enhanced, improving the sensitivity and limit of detection.

FIG. 7 schematically depicts a multi-pass sensor design that is compact and convenient to assemble. The deposited nanoparticle film and sample gas flow are disposed within an optical cavity between narrowly spaced mirrors. Light enters and exits at near-normal incidence to the nanoparticle-coated mirror. The active optical path length is no greater than the thickness of the plasmonic film (e.g., 5 nm).

According to various embodiments, a multi-pass system of the present teachings can make an absorbance measurement using the following number of film passes: 2 passes, 5 passes, 10 passes, 15 passes, 20 passes, 25 passes, 30 passes, 35 passes, or greater. In various embodiments, about 20-30 film-passes can be made within the dimensional and photonic specifications of the identified photonic front ends. According to various embodiments, a multi-pass design can provide up to about 20 times the plasmonic signal compared to a single-pass design. In some embodiments, a multi-pass design can provide up to about 30 times the plasmonic signal, or greater, compared to a single-pass design.

Notable feature considerations in a multi-pass design, as contemplated by various embodiments of the present teachings, include, for example, one or more of the following:

(1) To minimize losses in the cell, high reflectivity mirrors (e.g., enhanced aluminum (R>90%) or dielectric (R>95%)) can be employed in the optical cavity. This can substantially preserve the signal intensity through the transit of the cell.

(2) Collimated light can provide a narrower range of angles of incidence in the cell and allow for tighter control of the optical path.

(3) Using light that enters close to normal relative to the length of the optical cell can increase the number of passes. This is achieved in the above table (Table 1), for example, by increasing the distance from the light source and optical cell while keeping the other dimensions consistent.

All references set forth herein are expressly incorporated by reference in their entireties for all purposes.

Those skilled in the art can now appreciate from the foregoing description that the broad teachings herein can be implemented in a variety of forms. Therefore, while the present teachings have been described in connection with various embodiments and examples, the scope of the present teachings are not intended, and should not be construed to be, limited thereby. Various changes and modifications can be made without departing from the scope of the present teachings.

It is claimed:

1. An analyte detection system, comprising:
(a) a flow cell comprising a multi-pass plasmonic sensor;
   wherein the multi-pass plasmonic sensor comprises:
   (i) a first transparent substrate comprising a first mirrored surface; and an analyte-sensitive film disposed on a surface region of the first substrate, wherein the analyte-sensitive film comprises a plurality of metallic nanoparticles having an affinity for a selected analyte of interest;
   (ii) a second substrate comprising a second mirrored surface in confronting spaced relation, on the order of millimeters, proximate to the first mirrored surface; and
   (iii) a cavity region interposing the first and second mirrored surfaces;
(b) a light detector configured for detecting a localized surface plasmon resonance (LSPR) signal from the analyte-sensitive film
(c) a light source for directing a beam of light along a beam path that (i) enters the cavity region, (ii) impinges the analyte-sensitive film on the first substrate and reflects off the first mirrored surface, (iii) impinges and reflects off the second mirrored surface, (iv) again, impinges the analyte-sensitive film on the first substrate and reflects off the first mirrored surface, and (v) exits the cavity region enroute to the detector; and
(d) a temperature-control unit adapted to regulate the temperature of the analyte-sensitive film to a selected temperature;
   wherein, the system can determine whether the analyte is present in a sample based on a LSPR signal detected from the analyte-sensitive film.

2. The system of claim 1, wherein, following steps (c) (i) and (c) (ii), each of steps (c) (iii) and (c) (iv) occur multiple times before step (c) (v) takes place.

3. The system of claim 1, wherein the analyte comprises a heavy metal.

4. The system of claim 3, wherein the heavy metal comprises mercury.

5. The system of claim 1, wherein the nanoparticles comprise an alloy.

6. The system of claim 5, wherein the alloy comprises an amalgam.

7. The system of claim 1, wherein the nanoparticles are preconditioned to substantially preclude irreversible analyte adsorption during use with said sample at the selected temperature of the analyte-sensitive film.

8. The system of claim 1, further comprising a gas source in communication with the flow cell and configured to provide a flow of a gas through the flow cell; and further wherein the sample is a gaseous sample.

9. The system of claim 1, wherein the light source comprises a visible light source.

10. The system of claim 9, wherein the system is configured to detect changes in optical absorbance in a single active band of the visible light spectrum.

11. A method for determining whether a selected analyte is present in a gaseous sample, the method comprising:

(a) contacting a sample to an analyte sensor comprising:

(i) a first transparent substrate comprising a first mirrored surface; and an analyte-sensitive film disposed on a surface region of the first substrate, wherein the analyte-sensitive film comprises a plurality of metallic nanoparticles having an affinity for a selected analyte of interest;

(ii) a second substrate comprising a second mirrored surface in confronting spaced relation, on the order of millimeters, proximate to the first mirrored surface; and (iii) a cavity region interposing the first and second mirrored surfaces;

(b) regulating the temperature of the analyte-sensitive film to a selected temperature;

(c) while performing step (b):

(i) directing light along a first path extending through the transparent substrate into the cavity region and onto the analyte-sensitive film, then reflecting off the first mirrored surface and extending to the second mirrored surface, reflecting off the second mirrored surface onto the analyte-sensitive film again, and finally exiting the cavity region;

(ii) detecting a localized surface plasmon resonance (LSPR) signal from the analyte-sensitive film; and (d) determining whether the analyte is present in the sample based on a LSPR signal detected from the analyte-sensitive film.

12. The method of claim 11, wherein step (d) includes monitoring changes in transmission through the analyte-sensitive film in a single band or multiple bands of the visible spectrum.

13. The method of claim 11, wherein step (d) includes integrating detected steady-state LSPR signal with time.

14. The method of claim 11, further comprising the step of preconditioning the nanoparticles of the film to substantially preclude irreversible analyte adsorption during use with said sample at the selected temperature of the analyte-sensitive film.

15. The method of claim 11, wherein the analyte comprises a heavy metal.

16. The method of claim 15, wherein the heavy metal comprises mercury.

17. The method of claim 16, wherein the metallic nanoparticles comprise an amalgam.

18. The method of claim 11, wherein the sample comprises at least one of a gas or liquid.

* * * * *